(12) United States Patent
Li et al.

(10) Patent No.: US 9,051,375 B2
(45) Date of Patent: Jun. 9, 2015

(54) ALKALI-RESISTANT VARIANTS OF PROTEIN A AND THEIR USE IN AFFINITY CHROMATOGRAPHY

(75) Inventors: Shun-Cheng Li, London (CA); Xing Li, London (CA); Courtney Voss, London (CA); Satoshi Nakamura, Minato-ku (JP); Tetsuo Fukuta, Minato-ku (JP); Yusuke Okano, Minato-ku (JP); Tomonori Shiotani, Minato-ku (JP); Kouji Tamori, Minato-ku (JP); Yu Otani, Minato-ku (JP)

(73) Assignees: THE UNIVERSITY OF WESTERN ONTARIO, London (CA); JSR CORPORATION, Tokyo (JP)

( * ) Notice: Subject to any disclaimer, the term of this patent is extended or adjusted under 35 U.S.C. 154(b) by 0 days.

(21) Appl. No.: 13/997,015

(22) PCT Filed: Dec. 21, 2011

(86) PCT No.: PCT/CA2011/001370
§ 371 (c)(1),
(2), (4) Date: Sep. 23, 2013

(87) PCT Pub. No.: WO2012/083425
PCT Pub. Date: Jun. 28, 2012

(65) Prior Publication Data
US 2014/0031522 A1    Jan. 30, 2014

Related U.S. Application Data

(60) Provisional application No. 61/425,617, filed on Dec. 21, 2010.

(51) Int. Cl.
| | | |
|---|---|---|
| *C07K 14/31* | (2006.01) |
| *C07K 17/06* | (2006.01) |
| *C07K 1/22* | (2006.01) |
| *B01D 15/38* | (2006.01) |
| *B01J 20/32* | (2006.01) |
| *B01J 20/28* | (2006.01) |

(52) U.S. Cl.
CPC ............ *C07K 14/31* (2013.01); *B01D 15/3809* (2013.01); *C07K 1/22* (2013.01); *C07K 17/06* (2013.01); *B01J 20/3204* (2013.01); *B01J 20/3208* (2013.01); *B01J 20/3219* (2013.01); *B01J 20/3274* (2013.01); *B01J 20/28057* (2013.01); *B01J 20/28078* (2013.01)

(58) Field of Classification Search
None
See application file for complete search history.

(56) References Cited

U.S. PATENT DOCUMENTS

| | | | |
|---|---|---|---|
| 5,084,559 A | 1/1992 | Profy | |
| 5,260,373 A | 11/1993 | Profy et al. | |
| 5,831,012 A * | 11/1998 | Nilsson et al. | 530/350 |
| 6,013,763 A | 1/2000 | Braisted et al. | |
| 6,197,927 B1 | 3/2001 | Braisted et al. | |
| 6,534,628 B1 * | 3/2003 | Nilsson et al. | 530/350 |
| 6,740,734 B1 * | 5/2004 | Nilsson et al. | 530/350 |
| 6,831,161 B1 * | 12/2004 | Uhlen et al. | 530/413 |
| 7,485,704 B2 | 2/2009 | Fahrner et al. | |
| 7,709,209 B2 | 5/2010 | Hober et al. | |
| 7,834,158 B2 | 11/2010 | Hober | |
| 8,198,404 B2 | 6/2012 | Hober | |
| 8,354,510 B2 | 1/2013 | Hober et al. | |
| 2005/0100970 A1 * | 5/2005 | Uhlen et al. | 435/7.1 |
| 2006/0194950 A1 | 8/2006 | Hober et al. | |
| 2009/0099344 A1 | 4/2009 | Fahrner et al. | |
| 2010/0105879 A1 | 4/2010 | Katayose et al. | |
| 2010/0221844 A1 * | 9/2010 | Bian et al. | 436/501 |
| 2010/0286373 A1 | 11/2010 | Majima et al. | |
| 2012/0208234 A1 * | 8/2012 | Yoshida et al. | 435/69.1 |
| 2012/0238724 A1 | 9/2012 | Hober | |

FOREIGN PATENT DOCUMENTS

| | | | |
|---|---|---|---|
| CA | 2 347 960 | | 4/2000 |
| CA | 2347960 | * | 4/2000 |
| CN | 101632019 | | 1/2010 |
| CN | 101775069 | | 7/2010 |
| EP | 1992692 A1 | | 11/2008 |
| EP | 2 128 616 | | 12/2009 |
| EP | 2 202 310 | | 6/2010 |

(Continued)

OTHER PUBLICATIONS

Linhult, M. Protein engineering to explore and improve affinity ligands. Royal Institute of Tectmology, Department of Biotectmology, Stockholm, Sweden (cited in related PCT International Search Report/Written Opinion).*
U.S. Appl. No. 13/996,978, filed Jun. 21, 2013, Nakamura, et al.
Linhult, M., "Protein engineering to explore and improve affinity ligands", Royal Institute of Technology, Department of Biotechnology, Total 69 Pages, (2003).
International Search Report Issued May 3, 2012 in PCT/CA11/01370 Filed Dec. 21, 2011.
International Search Report Issued Mar. 6, 2012 in Related Application PCT/JP11/079568 Filed Dec. 20, 2011.

*Primary Examiner* — Maury Audet
(74) *Attorney, Agent, or Firm* — Oblon, McClelland, Maier & Neustadt, L.L.P.

(57) ABSTRACT

The present invention relates to immunoglobulin (Ig)-binding proteins with alkali-resistance properties. In one embodiment, the present invention provides for a variant of an Ig-binding protein, the variant comprising the Ig-binding protein having at least one asparagine residue substituted with a histidine, a serine, an aspartic acid or a threonine residue. The at least one substitution may confer to the variant Ig-binding protein an increased stability in alkaline solutions when compared to the wild-type Ig-binding. The present invention relates also to matrices for affinity separation of immunoglobulins comprising the Ig-binding proteins of the present invention, and to methods of using the Ig-binding proteins of the present invention to separate immunoglobulins from mixture compositions.

27 Claims, 4 Drawing Sheets

(56) References Cited

FOREIGN PATENT DOCUMENTS

| | | | |
|---|---|---|---|
| EP | 2202310 | * | 6/2010 |
| EP | 2202310 A2 | | 6/2010 |
| JP | 6 281638 | | 10/1994 |
| JP | 2006-304633 | * 11/2006 | ............. C12N 15/00 |
| JP | 2007-252368 | | 10/2007 |
| JP | 2008-214350 | | 9/2008 |
| JP | 2008 241560 | | 10/2008 |
| JP | 2010 156687 | | 7/2010 |
| WO | 95 19374 | | 7/1995 |
| WO | WO9519374 | * | 7/1995 |
| WO | 2007/097361 | | 8/2007 |
| WO | 2008 117638 | | 10/2008 |
| WO | 2010 035756 | | 4/2010 |
| WO | 2010/110288 | | 9/2010 |

* cited by examiner

ALKALI-RESISTANT VARIANTS OF PROTEIN A AND THEIR USE IN AFFINITY CHROMATOGRAPHY

FIELD OF THE INVENTION

This invention relates to several immunoglobulin (Ig)-ligand proteins with alkali-resistance properties, their immobilization to a solid support, and the application of the resulting affinity matrix in Ig purification.

BACKGROUND OF THE INVENTION

Protein A is a membrane protein encoded by a bacterium (*Staphylococcus aureus*). Protein A consists of five homologues domains arranged as E-D-A-B-C. Protein A is unique in its ability to bind to most antibodies (including IgG, IgM, IgE, IgA) from various species including humans. Thus, Protein A has been widely used as a protein ligand immobilized on a solid support (eg., resin) to form an affinity column for antibody purification for research and therapeutic applications.

To fully exploit the antibody-binding property of Protein A for both pharmaceutical and biotechnological applications, methods to improve the immobilization efficiency of Protein A on a solid resin, as well as methods of increasing protein A stability and reducing its leakage after immobilization have been under investigation. In this regard, U.S. Pat. Nos. 5,084,559 and 5,260,373 describe methods of immobilizing Protein A in which a single cysteine residue, or a single arginine residue, is added to the N-terminus of Protein A, or a domain, or multiple domains thereof, to facilitate their immobilization. Methods to stabilize the immobilized protein have also been described in U.S. Pat. No. 7,485,704 in which Protein A ligand leakage is alleviated by reducing temperature during the antibody purification, and in US patent (U.S. Pat. No. 7,709,209) in which alkali stability of a protein A domain is increased by mutating specific asparagine residues in its sequence to an amino acid other than glutamine or aspartic acid.

Despite the foregoing, there remains a need to develop improved methods for protein immobilization and enhanced ligand stability.

Affinity chromatography is one of the most useful separation methods to purify proteins with high recovery rate in a single step. Epoxy-based coupling is a widely used technology for peptide or protein immobilization. The epoxy group contains an oxygen atom joined by single bonds to two adjacent carbon atoms to form an epoxide ring. This functional group is able to react with different nucleophilic groups on a protein surface to form a strong linkage with minimal chemical modifications. However, the immobilization efficiency on epoxy resin is largely dependent on the composition of a given peptide or protein, including amino acid sequence, pI and protein secondary structures, as well as reaction conditions including pH, coupling buffer composition and salt concentration.

SUMMARY OF THE INVENTION

In one embodiment, the present invention provides for a variant of an immunoglobulin (Ig)-binding protein, said variant comprising the Ig-binding protein having at least one asparagine (Asn) residue in the Ig-binding protein substituted with a histidine (His), a serine (Ser), an aspartic acid (Asp) or a threonine (Thr) residue, wherein said at least one substitution confers the variant with increased alkali stability properties when compared to the Ig-binding protein.

In one embodiment, the present invention provides for a matrix for affinity separation, characterized in that the matrix comprises a variant of an immunoglobulin (Ig)-binding protein coupled to a solid support, said variant comprising the Ig-binding protein having at least one Asn residue in the Ig-binding protein has been substituted with a His, a Ser, an Asp or a Thr residue, said at least one substitution conferring the variant with increased alkali stability properties when compared to the Ig-binding protein.

In one embodiment, the present invention provides for a method of separating immunoglobulins (Igs) from a composition, the composition comprising the Igs and at least one other substance from which the Igs are to be separated, characterized in that said method comprises contacting the composition with a matrix for affinity separation, the matrix comprising a variant of an Ig-binding protein coupled to a solid support, thereby separating the Igs from the at least one other substance in the composition, said variant comprising the Ig-binding protein having at least one Asn residue in the Ig-binding protein has been substituted with a His, a Ser, an Asp or a Thr residue, said at least one substitution conferring the variant with increased alkali stability properties when compared to the Ig-binding protein.

In one embodiment of the present invention the variant Ig-binding protein is protein A.

In another embodiment of the present invention the Ig-binding protein comprises an amino acid sequence of SEQ ID NO: 1.

In another embodiment of the present invention the variant Ig-binding protein comprises the Ig-binding protein comprising the amino acid sequence of SEQ ID NO: 1 having an Asn3His (asparagine residue at position 3 of SEQ ID. NO: 1 substituted with a histidine residue) substitution or an Asn3Ser substitution.

In another embodiment of the present invention the variant Ig-binding protein comprises the Ig-binding protein comprising the amino acid sequence of SEQ ID NO: 1 having an Asn6Asp substitution.

In another embodiment of the present invention the variant Ig-binding protein comprises the Ig-binding protein comprising the amino acid sequence of SEQ ID NO: 1 having an Asn23Ser substitution.

In another embodiment of the present invention the variant Ig-binding protein comprises the Ig-binding protein comprising the amino acid sequence of SEQ ID NO: 1 having a double substitution selected from Asn3His/Asn23Ser or Asn3His/An23Thr.

In another embodiment of the present invention the variant Ig-binding protein comprises the Ig-binding protein comprising the amino acid sequence of SEQ ID NO: 1 having a triple substitution Asn3His/Asn6Asp/Asn23Ser.

In another embodiment of the present invention the variant Ig-binding protein comprises the Ig-binding protein having 4 tandems of SEQ ID. NO: 8.

In another embodiment the present invention the variant Ig-binding protein protein comprises the Ig-binding protein having at least one Asn residue substituted with an Asp residue.

In another embodiment the present invention is a variant Ig-binding protein characterized in that said variant is coupled to a linker peptide capable of immobilizing the variant to a matrix for affinity separation. In aspects of the invention the linker peptide comprises the amino acid sequence of SEQ ID NO: 15.

In another embodiment the present invention is a variant Ig-binding protein characterized in that said Ig-binding protein is selected from SEQ ID NOs.: 2-11 and 14.

These embodiments and other aspects of the invention will become apparent from the detailed description by reference to the following Figures.

DETAILED DESCRIPTION OF THE INVENTION

Definitions

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

The term "functionally equivalent derivative" is used herein to refer to derivatized versions which retain the function of anchor to immobilize the selected protein without substantial loss of protein function.

The term "ligand" as used herein refers to a molecule or group of molecules that bind to one or more specific sites of a receptor.

Overview

Figure 3:
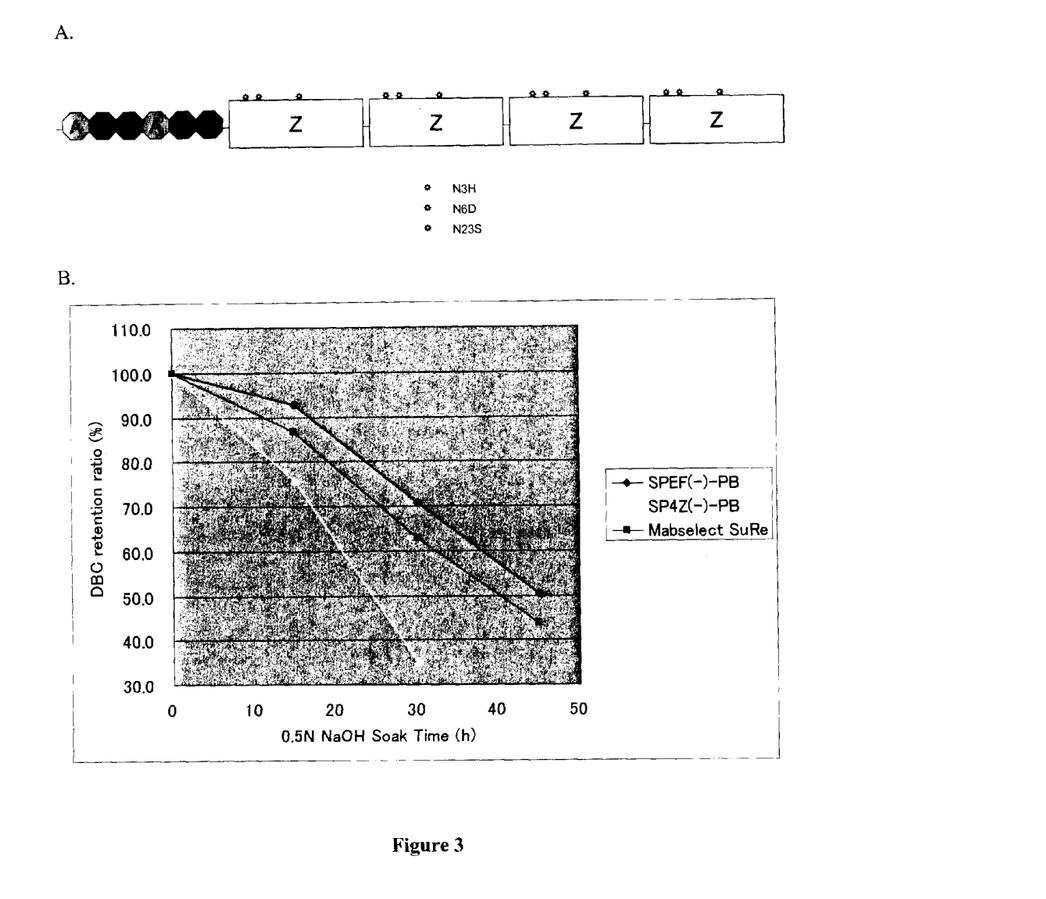
FIG. 3 illustrates the dynamic binding capacity retention ratio of three affinity columns, the first containing immobilized 4DHS (four tandem repeats of the DHS mutant of the Z domain), the second containing immobilized X03 (four Z domain repeat) and the third containing MabSelect SuRe™ beads (GE Healthcare) upon soaking for different durations in 0.5N NaOH.

This invention relates to several immunoglobulin (Ig)-ligand proteins with alkali-resistance properties. In one embodiment, the present invention relates to a variant of an immunoglobulin (Ig)-binding protein, in which at least one asparagine (Asn) residue of the wild-type or parental Ig-binding proteins is substituted with a histidine (His), a serine (Ser), an aspartic acid (Asp) or a threonine (Thr) residue. As illustrated in FIG. 3 B, the at least one substitution may confer to the variant Ig-binding protein an increased stability in alkaline solutions when compared to the wild-type Ig-binding.

The present invention relates also to novel amino acid sequences and to novel Ig-binding proteins. In one embodiment of the present invention the novel Ig-binding proteins may be selected form SEQ ID NOs: 2-11 and SEQ ID NO: 14.

The Ig-ligand protein of the present invention may be an Fc-fragment-binding protein, and may be used for selective binding of IgG, IgA and/or IgM, preferably IgG.

The Ig-Binding Protein Variant

In one embodiment, the present invention relates to a variant of an immunoglobulin (Ig)-binding protein. The variant may comprise the Ig-binding protein having at least one Asn residue substituted with a His, a Ser, an Asp, or a Thr residue. The at least one substitution may confer to the variant Ig-binding protein with increased stability in alkaline solutions when compared to the wild-type Ig-binding.

In one embodiment, the present invention relates to an Ig-binding protein with increased stability in alkaline solutions when compared to protein A. The Ig-binding protein of the present invention may comprise the protein A having at least one Asn residue of the Z domain or B domain of the protein A substituted with a His, a Ser, an Asp, or a Thr residue.

In one embodiment, the Ig-binding protein of the present invention may comprise a protein A having single, double or triple substitutions, such as mutations, on Asn3 (i.e. asparagine in position 3), Asn6 and Asn23 in the Z domain (SEQ ID NO: 1) or the B domain of protein A. The single substitution may be selected from Asn3His (i.e. asparagine in position 3 substituted with or mutated to histidine), Asn3Serine, Asn6Asp, Asn23His or Asn23Ser, the double substitution may be selected from Asn3His/Asn23Ser or Asn3His/Asn23Thr, and the triple mutation may be Asn3His/Asn6Asp/Asn23Ser.

In one embodiment, the Ig-binding protein of the present invention may be modified by recombinant means to include a spacer or linker sequence as either an N- or C-terminal extension and thereby form a fusion protein-linker product, which may confer improved immobilization to a solid support. In this regard, as one of skill in the art will be appreciated, the linker or spacer may be chemically synthesized and covalently bound to the selected Ig-binding protein using well-established methodologies. Alternatively, a fusion product comprising the linker and the Ig-ligand of the present invention may be made using recombinant technology. In this regard, the linker may be generally bound or fused to a terminus of the Ig ligand such that the function of the Ig ligand may be substantially retained. Thus, depending on the protein, the linker may be bound to the N-terminus or the C-terminus of the Ig ligand. In certain instances, the linker may be bound to both termini, or may additionally be bound to an amino acid residue which is not a terminal residue. In another alternative, the linker may be bound to a solid support prior to the coupling of the Ig-binding protein by chemical or recombinant means or through the use of an enzyme.

The linker may be suitable to immobilize the Ig-binding protein of the present invention onto a solid support while substantially retaining the function of the Ig-binding protein, i.e. retaining at least about 50% of immunoglobulin binding, in its immobilized state.

US Pat. Appl. No. 2007/0055013 provides an example of a linker that may be fused to the Ig-ligand of the present invention.

It is further contemplated that the present invention encompasses vectors which comprise nucleic acids coding for the Ig-binding proteins of the present invention, or nucleic acids coding for the Ig-binding proteins fused to a linker.

The Ig-binding proteins of the invention may be labelled with a label to facilitate their detection in an Ig separation assay as is understood by one of skill in the art. Such labels may include but are not limited to radioactive label and fluorescent label. The Ig-binding proteins of the invention may be provided with a carrier such as for example coupled to bovine serum albumin (BSA) or keyhole limpet haemocyanin.

The Solid Support

Figure 2:
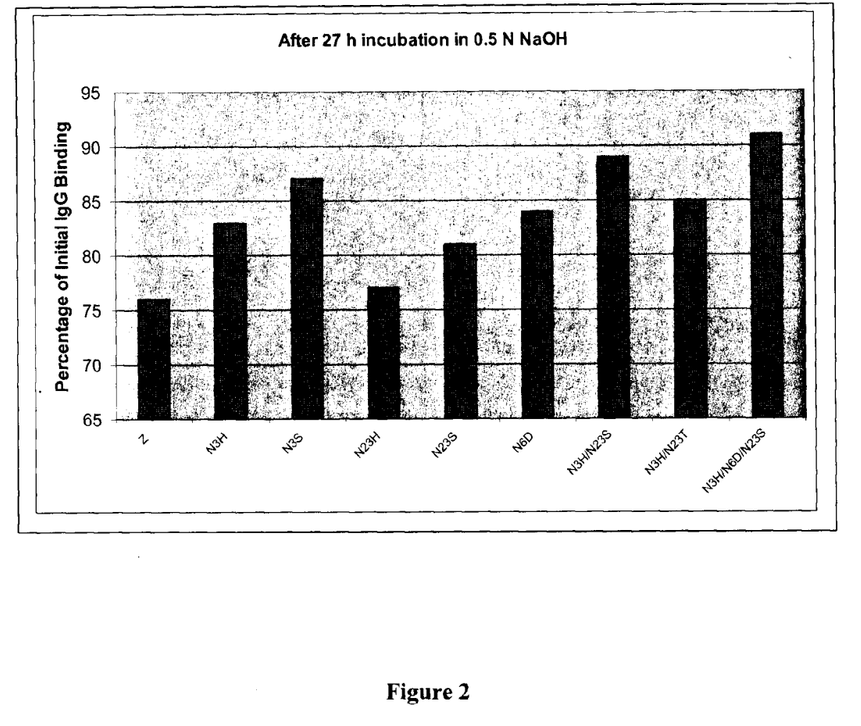
FIG. 2 illustrate the remaining IgG-binding capacity of different mutants of the Z domain after 27 hours of continuous incubation in 0.5 NaOH, in comparison to the Z domain itself used as a control.

In one embodiment, the present invention relates to a matrix for affinity separation. The matrix may comprise Ig-ligands that may be made of any of the Ig-binding protein of the present invention coupled to a solid support. As illustrated in FIG. 2, a matrix according to embodiments of the present invention, when compared to a matrix comprised of the parental molecule as Ig-ligand (Z in FIG. 2), exhibits an increased binding capacity during two or more separations with intermittent alkaline cleaning. The inventors unexpectedly found that mutating an asparagine residue to aspartic acid (D) confers the Ig-ligand with improved binding capacity. The Ig-ligand protein of the present invention may preferably be an Fc-fragment-binding protein, and may be used for selective binding of IgG, IgA and/or IgM, preferably IgG.

Once the ligand protein is bound or fused to the anchor peptide, the fused product may be coupled (covalently or non-covalently) onto a solid support. Suitable solid supports include epoxy-based supports, e.g. beads or resins, or solid supports having the surface chemistry of an epoxy group, or materials that are functionalized on the surface to allow coupling of a protein via the anchor sequence.

Examples of the material for the solid support is based on polymers having hydrophilic surface, such as polymers having hydroxyl group (—OH), carboxyl group (—COOH), aminocarbonyl group (—CONH$_2$, possibly in N-substituted forms), amino group (—NH$_2$, possibly in substituted form), oligo or polyethyleneoxy group on their external surface and if present, also on internal surface. In one embodiment, the polymer is a synthetic polymer (e.g., polymethacrylate, polyacrylamide, or styrene-divinylbenzene copolymer). Such a synthetic polymer may be easily produced by a known method (see J. MATER. CHEM 1991, 1(3), 371-374, for example). Alternatively, a commercially available product such as TOYOPEARL (manufactured by Tosoh Corp.) may also be used. In another embodiment, the polymer is a polysaccharide (e.g., dextran, starch, cellulose, pullulan, or agarose). Such a polysaccharide may be easily produced by a known method (see Japanese Patent No. 4081143, for example). Alternatively, a commercially available product such as Sepharose (manufactured by GE Healthcare Biosciences) may also be used. In still another embodiment, an inorganic support (e.g., silica or zirconium oxide) may be used.

To immobilize the Ig-ligand protein of the present invention or a fused product to the solid support, the solid support may be treated in an aqueous solution. The aqueous solution may comprise a binding buffer, e.g. 0.1 M sodium phosphate/ 0.5 M Na$_2$SO$_4$, pH, e.g. in the range of about 6.5 to 7.2, preferring pH 6.8. Suitable salts for use in this regard include salts that are compatible with the solid support and fused product, non-toxic with regard to the intended use of the immobilized protein and otherwise suitable for use. The solid support may be mixed with the Ig-ligand peptide, for example at about room temperature, for a sufficient period of time for immobilization to occur.

The solid support may be in the shape of particles. The particles may be porous or nonporous. The solid support in the shape of particles may be used as a packed bed, or may be used in a suspended form. The suspended form may be an expanded bed or a pure suspension, in which the particles can move freely. When using a packed bed, or an expanded bed, separation process used in known affinity chromatographic methods may be used. When using a pure suspension, a batch method is used.

The solid support in the shape of particles according to this embodiment preferably may have a particle size (volume average particle size) of about 20 to about 200 micrometers, and more preferably about 30 to about 100 micrometers. If the solid support has a particle size of less than about 20 micrometers, the pressure of column packed with this support may increase to an impractical level at a high flow rate. If the solid support has a particle size of more than about 200 micrometers, the binding capacity may deteriorate. Note that the term "particle size" used herein refers to a volume average particle size determined using a laser diffraction/scattering particle size distribution analyzer.

The solid support according to this embodiment may preferably be porous, and may have a specific surface area larger than about 50-1000 m$^2$/g-, and more preferably about 80 to about 400 m$^2$/g. If the affinity chromatography packing material has a specific surface area of less than about 50 m$^2$/g, the binding capacity may deteriorate. If the affinity chromatography packing material has a specific surface area of more than about 1000 m$^2$/g, the packing material may be destroyed at a high flow rate due to a decrease in strength, so that the column pressure may increase. Note that the term "specific surface area" used herein refers to a value of the surface area of pores (pore size: about 10 to about 5000 nm) determined using a mercury porosimeter by the dry weight of the particles.

The solid support according to this embodiment may have a volume average pore size of about 50 to about 400 nm, and more preferably about 100 to about 300 nm. If the affinity solid support has a volume average pore size of less than about 50 nm, the binding capacity may significantly deteriorate at a high flow rate. If the affinity chromatography packing material has a volume average pore size of more than about 400 nm, the binding capacity may deteriorate irrespective of the flow rate. Note that the term "volume average pore size" used herein refers to the volume average pore size of pores (pore size: 10 to 5000 nm) determined using a mercury porosimeter.

Specific examples of porous particles used as the solid support according to this embodiment include porous organic polymer particles including a copolymer of 20 to 50 wt % of a crosslinkable vinyl monomer, 3 to 80 wt % of an epoxy group-containing vinyl monomer, and 20 to 80 wt % of a diol group-containing vinyl monomer, and having a particle size of 20 to 80 micrometers, a specific surface area of 50 to 150 m$^2$/g, and a volume average pore size of 100 to 400 nm.

In yet another form embodiment, the solid support may be in another form such as a surface, a monolith, a chip, capillaries, or a filter.

The Ig-binding protein of the present invention may be attached to the support via conventional coupling techniques utilizing, e.g. amino and/or carboxy groups present in the ligand. Bisepoxides, epichlorohydrin, CNBr, N-hydroxysuccinimide (NHS) etc are well-known coupling reagents. Between the support and the ligand, a molecule known as a spacer or linker may be introduced, which will improve the availability of the Ig-binding protein and facilitate the chemical coupling of the Ig-binding protein to the support. Alternatively, the Ig-binding protein may be attached to the support by non-covalent bonding, such as physical adsorption or biospecific adsorption.

In one embodiment, the Ig-ligands of the present invention may be coupled to the support by imino (—NH—) bonds. Methods for performing such coupling are well-known in this field and easily performed by the person of ordinary skill in this field using standard techniques and equipment. In an advantageous embodiment, the ligand may be firstly provided with one or more terminal lysine residues for subsequent use in the coupling. The person of ordinary skill in this field may also easily perform appropriate steps of purification.

As mentioned above, the affinity to immunoglobulin i.e. the binding properties of the present ligand, and hence the capacity of the matrix, may not essentially be changed in time by treatment with an alkaline agent (i.e. alkaline resistant). Conventionally, for a cleaning in place treatment of an affinity separation matrix, the alkaline agent used may be NaOH and the concentration thereof is up to about 0.8 M, such as about 0.5 M.

Methods of Use

In one embodiment, the present invention relates to methods of separating immunoglobulins (Igs), such as IgG, IgA and/or IgM, or Fc-fusion protein, from a composition. The composition may be comprised of the Igs and at least one other substance from which the Igs are to be separated. The method may comprise contacting the composition with a matrix for affinity separation, the matrix comprising a variant or mutant Ig-binding protein according to embodiments of the present invention, a multimer or a matrix according to the present invention coupled to a solid support, thereby separating the Igs from the at least one other substance in the composition. The method may further comprise eluting the Igs from the solid support by adding an eluent to the matrix.

The present method provides reliable immobilization of proteins, in particular immunoglobulin-binding proteins, for use in the preparation of affinity columns having utility in the isolation of ligands that bind to the immobilized protein, e.g. immunoglobulins such as IgG, IgG1, IgG2, IgM, IgA and IgE.

Embodiments of the invention are described in the following specific example which is not to be construed as limiting.

EXAMPLES

Example 1

Z Domain Site-Directed Mutations and Alkaline Resistance Evaluation

The Z domain (SEQ ID NO: 1), a variant of the B domain of Protein A of *Staphylococcus aureus*, were used as the templates to create mutants that contain site-specific mutations of one, two or three amino acid residues by Quickchange (Stratagene) mutagenesis. The Z domain mutants were cloned into a pETM11 expression vector that is equipped with a (His)6-tag to facilitate protein purification on a Nickel affinity column (Qiagen). Purified Z domain mutants were immobilized onto the epoxy-activated resin of GE Healthcare or the proprietary epoxy resin as shown in '(5). Synthesis of porous beads' section. The IgG-binding capacities and alkali-resistance ability of each Z domain mutants were evaluated as described below.

Figure 1:
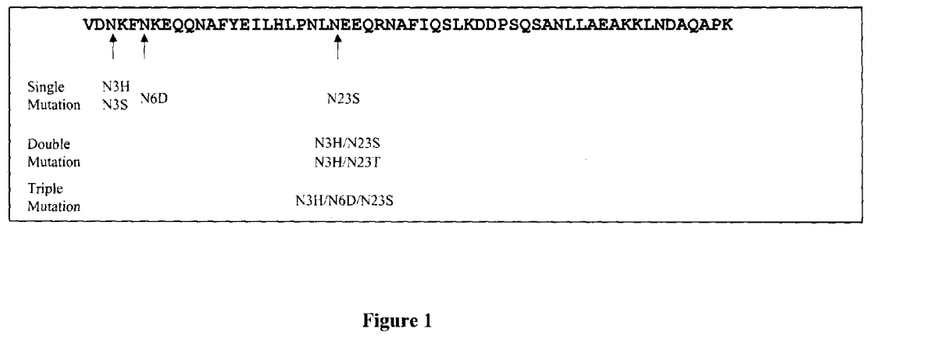
FIG. 1 depicts a sequence of the Z domain (SEQ ID NO: 1) and various mutants created in this invention.

To evaluate the alkali-resistance of the Z domain mutants, each mutant protein was expressed in *E. Coli* and purified on a Nickel affinity column followed by FPLC. The purified protein (>90% pure based on FPLC) was immobilized on epoxy-resin to create an affinity column. A Z mutant-affinity column was incubated in 0.5 NaOH for different period of time. After 27 hours incubation in the alkali solution, the column was washed thoroughly with PBS to bring the pH back to neutral. Then, human polyclonal IgG was loaded onto the column. After washing 3× with PBS, the bound IgG was eluted from the column in a pH 3.2 elution buffer. The eluted IgG sample was measured for UV absorbance at 280 nm to quantify the column's IgG binding capacity. The IgG-binding capacity was measured before and at different time points during alkali treatment. The Z domain mutants created in this invention are shown in FIG. 1, and the evaluation results shown in Table 1 and FIG. 2. Mutations of one or more Asn to His, Ser, and Asp, individually or in various combinations allowed for the creation of a panel of single, double or triple site Z domain mutants that show better alkali resistance than the parent Z domain (Table 1 and FIG. 2).

TABLE 1

Remaining IgG-binding capacity of Z domain mutants after 27 hours of incubation in 0.5N NaOH

| Ig-binding protein | IgG-binding capacity at 27 h (%) |
|---|---|
| Z (SEQ ID NO: 1) | 76 |
| N3H (SEQ ID NO: 2) | 83 |
| N3S (SEQ ID NO: 3) | 87 |
| N23H (SEQ ID NO: 4) | 78 |
| N23S (SEQ ID NO: 5) | 81 |
| N3H/N23S (SEQ ID NO: 6) | 89 |
| N3H/N23T (SEQ ID NO: 7) | 85 |
| N6D (SEQ ID NO: 14) | 84 |
| N3H/N6D/N23S (SEQ ID NO: 8) | 91 |

Example 2

Figure 4:
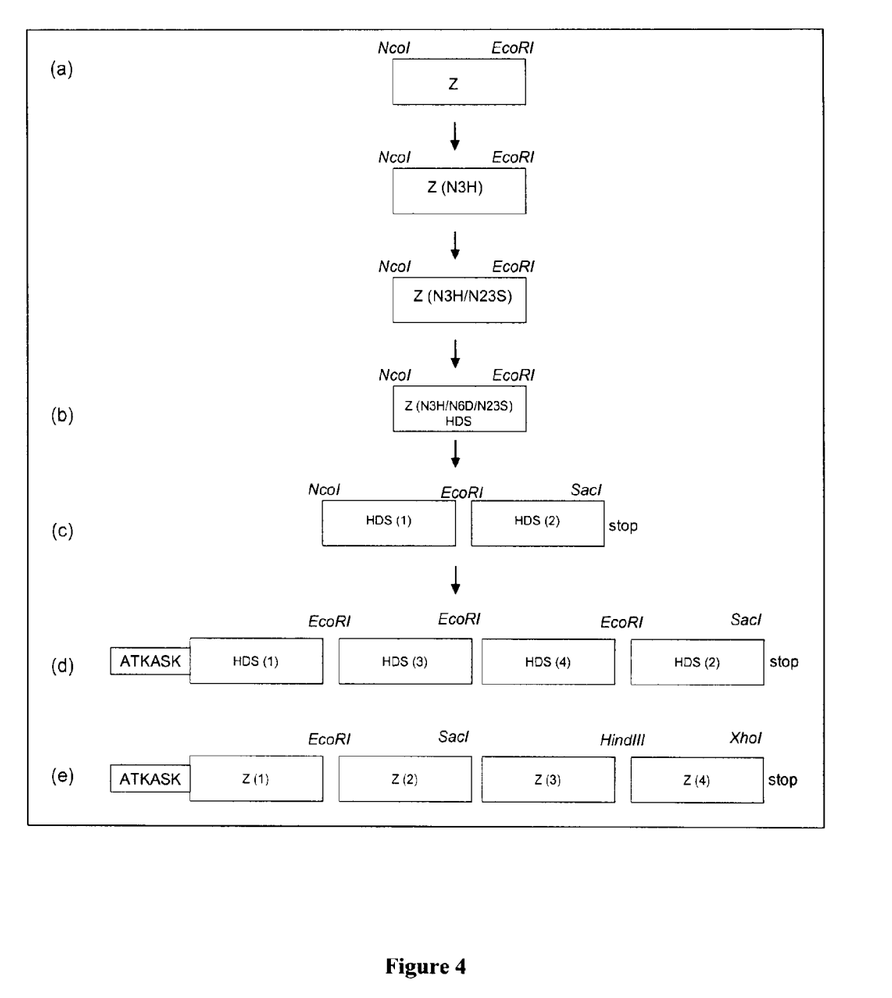
FIG. 4 outlines the procedures used to clone the 4 domain repeats of the protein A domain Z or the triple mutant of domain Z, HDS. This figure includes the sequence ATKASK (SEQ ID NO: 15).

Construction of Expression Vectors for 4 Tandem Copies of the Z Domain and the Triple Mutant N3H/N6D/N23S or 4HDS A flowchart of the cloning procedure is provided in FIG. 4. The wild-type Z domain (FIG. 4 (*a*)) (ligated in pETM11 with NcoI-EcoRI) was used as the building block to create the 4HDS (4 tandem copies of Z domain and the tripe mutant N3H/N6D/N23S) construct.

The N3H/N6D/N23S mutations were introduced consecutively into the Z domain using the Quickchange PCR protocol (Stratagene) to create a single copy of HDS (SEQ ID NO: 8) (FIG. 4 (*b*)). The presence of the mutations was verified by DNA sequencing.

Next, 2×HDS domains with a terminating stop codon were created by insertion of a second HDS domain using EcoRI and SacI as the flanking restriction sites (FIG. 4 (*c*)).

The 4×HDS domain (SEQ ID NO: NO. 10) construct was created by insertion of two copies of an EcoRI-EcoRI HDS domain.

The NcoI site at the N-terminus of the construct was removed and the linker sequence (ATKASK, SEQ ID NO: 15) was inserted using Quickchange PCR to create the final 4×HDS plasmid (FIG. 4 (*d*)). This 4×HDS sequence was then subcloned into the pET24a vector (Novagen) using NdeI-XhoI restriction enzymes.

X03, 4 tandem repeats of the Z domain, was constructed in a similar manner, but some domains were inserted using alternative restriction enzyme sites (FIG. 4 (*e*)).

The sequence of the final protein product of the 4×HDS construct is provided below.

AMINO ACID SEQUENCE OF 4HDS (Mutated residues identified in double underline; inter-domain residues from cloning identified in underline; N-terminal extension identified by bold underline, SEQ ID NO: 9)

matkaskvdhkfdkeqqnafyeilhlpnlseeqrnafiqslkddpsqsa nllaeakklnd aqapkefvdhkfdkeqqnafyeilhlpnlseeqrnafiqslkddpsqsa nllaeakklnd -continued aqapke_f_vdhk_f_dkeqqnafyeilhlpnlgeeqrnafiqslkddpsqsa nllaeakklnd aqapke_f_vdhk_f_dkeqqnafyeilhlpnlgeeqrnafiqslkddpsqsa nllaeakklnd aqapk*

Methods and Materials For Examples 1 and 2

(1). Construct Protein A Expression Vectors—All constructs were expressed in either pETM11 vector (European Molecular Biology Laboratory) or pET24a vector (Novagen). The original Protein A gene was amplified by PCR method using a TAP-Tag plasmid (EMBL) containing Protein A gene as a template. The Z domain was created by the PCR assisted site-directed mutagenesis (see below).

The Protein A gene was amplified with Phusion polymerase (0.5 units, New England Biolabs, Ipswich, Mass., USA). The PCR conditions were as follows: 94° C. for 1 minute, 25 cycles of 94° C. for 30 seconds, 55° C. for 30 seconds and 72° C. for 2.5 minutes followed by a final elongation step at 72° C. for 10 minutes. Ligation reactions were conducted at room temperature for 16 hours using T4 DNA ligase (0.5 units, Invitrogen, Carlsbad, Calif., USA). The products of these reactions were then used for transformation of E. coli DH5α (F-endA1 glnV44 thi-1 recA1 relA1 gyrA96 deoR nupG lacZΔM15 hsdR17 λ-), and the cells were then mixed with SOB media (composition: 20 g of Tryptone, 5 g of yeast extracts per liter, 10 mM NaCl, 2.5 mM KCl, 10 mM $MgCl_2$, mM $MgSO_4$). Following transformation, the cells were then spread on a plate of an LB-agar culture medium containing LB media (composition: 10 g of tryptone, 5 g of yeast extracts, 10 g of sodium chloride per liter), 1.2% agar and 30 μg/mL of kanamycin, and cultured overnight at 37° C. Colony PCR was conducted to confirm the presence of the insert by placing one colony into 2 mL of LB media and incubating at 37° C. overnight. PCR was conducted the next day using 3 μL of the culture as a template, T7 Promoter (5'-TAATACGACTCACTATAGGG-3') (SEQ ID NO: 16) as a sense primer and T7 Terminator (5'-GCTAGTTATTGCTCAGCGG-3') (SEQ ID NO: 17) as an antisense primer. The PCR conditions were the same as above but with Taq polymerase (0.375 units, Fermentas, Burlington, ON, Canada). DNA containing the desired insert was then purified using a DNA miniprep kit (GE Healthcare, Baie d'Urfe, QC, Canada).

DNA cloning was performed in Escherichia coli DH5α for plasmid DNA amplification and sequencing. E. coli BL21 (DE3) (Invitrogen) was used for expression of recombinant proteins. E. coli was routinely grown in Luria Bertani broth at 37° C. with shaking at 200 rpm. Ampicillin or kanamycine (100 μg/ml) were incorporated into the medium where appropriate.

(2) Recombinant Protein Expression and Purification—BL21(DE3) pLysS competent cells allow high-efficiency protein expression of any gene that is under the control of a T7 promoter and has a ribosome binding site. BL21(DE3)pLysS is lysogenic for λ-DE3, which contains the T7 bacteriophage gene I, encoding T7 RNA polymerase under the control of the lac UV5 promoter. BL21(DE3)pLysS also contains a plasmid, pLysS, which carries the gene encoding T7 lysozyme. T7 lysozyme lowers the background expression level of target genes under the control of the T7 promoter but does not interfere with the level of expression achieved following induction by IPTG. Target DNA plasmids were used to transfect BL21 competent cells. 0.5 μl of plasmid DNA containing about 0.5 μg of DNA was used for transfection. The BL21 competent cells were stored at −80° C. An aliquot of BL21 cells (20 μl) was thawed and put on ice. 0.5 μl of plasmid DNA was mixed with the competent cells and put on ice for 60 minutes. After incubation on ice, these cells containing plasmid DNA were "heat shocked" in 45° C. water batch for 45 seconds and immediately put on ice for another 2 minutes. Then, 30 μl of LB medium was added to the bacterial cells and shaked at 37° C. for 1 hour. These cells were then spread on agar/LB plates containing kanamycine (final concentration: 100 μg/ml). These plates were incubated at 37° C. overnight.

For expression of recombinant Protein A domains, the DNA plasmids were transformed into E. coli BL21. Overnight cultures were inoculated into fresh medium and grown to an OD600 (optical density at 600 nm) of approximately 0.5. Isopropyl beta-D-1-thiogalactopyranoside (IPTG) was added to a concentration of 1 mM, and the culture was grown for a further 15 hours at 18° C. Cells were harvested by centrifugation at 7,000 rpm for 10 min in a Sorvall GS-3 rotor.

The pellet was resuspended in phosphate-buffered saline (PBS) containing protease inhibitor (Roche Applied Science), lysozyme (200 μg/ml), and DNase I (3 μg/ml). Cells were lysed by repeated freeze/thaw cycles. Cell debris was removed by centrifugation.

Recombinant proteins expressed in pETM11 vector contained an amino-terminal His-Tag. His-Tag fusion proteins were purified using the Ni-NTA columns (Qiagen) and dialyzed against PBS.

Recombinant protein expressed in pET24a vector did not contain His-Tag. The expressed fusion proteins were purified using human IgG affinity columns.

(3) PCR-Assisted Site-Directed Mutagenesis—Mutations were introduced into the Z or B domain using a PCR-based site-specific mutagenesis method. Briefly, overlapping oligonucleotides carrying the desired mutation were combined with appropriate flanking primers to yield two overlapping mutant products. Mutated domains were subcloned directionally into appropriate expression vectors. All mutations were confirmed by DNA sequencing.

(4) Protein Analysis by Polyacrylamide Gel Electrophoresis (SDS-PAGE)—Electrophoresis was performed on polyacrylamide gels in the presence of sodium dodecyl sulphate (SDS). Samples (10 μl) were mixed with 10 μl of sample buffer (62.5 mM Tris-HCl, pH 6.8, 2% SDS, 5% mercaptoethanol, 10% glycerol and 0.0025% brophenol blue), heated at 90° C. for 2 min, cooled and loaded on gels. Electrophoresis was performed at 75 mA in an apparatus purchased from Bio-Rad. Gels were stained in a solution of 0.5 mg/ml Coomassie blue in 5:5:1 methanol/water/acidic acid and de-stained in water heated in a microwave.

(5). Synthesis of Porous Beads—8.2 g of glycidyl methacrylate (manufactured by Mitsubishi Rayon Co., Ltd.), 65.9 g of trimethylolpropane trimethacrylate (manufactured by Sartomer), and 90.6 g of glycerol monomethacrylate (manufactured by NOF Corporation) were dissolved in 245.8 g of 2-octanone (manufactured by Toyo Gosei Co., Ltd.) and 62 g of acetophenone (manufactured by Wako Pure Chemical Industries, Ltd.), and 2 g of 2,2'-azoisobutyronitrile (manufactured by Wako Pure Chemical Industries, Ltd.) was added to the solution to prepare an organic monomer solution.

8.5 g of polyvinyl alcohol ("PVA-217" manufactured by Kuraray Co., Ltd.), 0.43 g of sodium dodecyl sulfate ("Emal 10G" manufactured by Kao Corporation), and 21.3 g of sodium sulfate (manufactured by Wako Pure Chemical Industries, Ltd.) were added to 4240 g of distilled water. The mixture was stirred overnight to prepare an aqueous solution.

A separable flask (7 l) was charged with the resulting aqueous solution. The separable flask was equipped with a thermometer, a stirring blade, and a cooling tube, and placed on a hot water bath. The aqueous solution was stirred at 600 rpm in a nitrogen atmosphere. When the temperature of the aqueous solution had reached 85° C., the organic monomer solution was added to the aqueous solution using a dropping funnel. The mixture was stirred for 5 hours.

After cooling the reaction solution, the reaction solution was transferred to a polypropylene bottle (5 l). The reaction solution was allowed to stand until the beads floated. Unnecessary water was then sucked out from the bottom of the bottle. Acetone was then added to the reaction solution to precipitate the beads. After allowing the reaction solution to stand for 3 minutes, acetone was removed by decantation. After repeating this operation twice, water was added to precipitate the beads. After allowing the mixture to stand for 3 minutes, the mixture was subjected to decantation. After replacing the dispersion medium of the bead dispersion with acetone, the mixture was air-dried overnight. The mixture was then dried using a vacuum dryer to obtain 90 g of porous beads (hereinafter referred to as "PB"). The average particle size of the PB was 43 micrometers, and the specific surface area of the PB was 83 $m^2/g$.

(6). Preparation of 4HDS with His Tag (4HDS(+))—4 copies of the HDS mutant of protein A domain Z are cloned into a modified form of the pETM-11 vector that encodes a histidine tag before the multi-cloning sites. When expressed in E. coli, the pETM-4HDS construct produces a protein of having the sequence shown in SEQ ID NO: 10. This protein, called 4HDS(+), features an N-terminal (His)7 tag, a Tev cleavage sequence ENLYFQG (SEQ ID NO: 18) and an ATKASK (SEQ ID NO: 15) linker (anchor). Two interdomain residues, EF (in green), are derived from the EcoRI restriction sites used for cloning (FIG. 4).

(7). Preparation of 4HDS without His Tag (4HDS (-))—As noted above, the 4HDS(+) protein contains an Tev cleavage site at the N-terminus. The TEV protease is a highly site-specific cysteine protease that is found in the tobacco etch virus (TEV). An optimal recognition sequence for this enzyme is Glu-Asn-Leu-Tyr-Phe-Gln-(Gly/Ser) (or ENLYFQ(G/S)) (SEQ ID NO: 19) and cleavage occurs between the Gln and Gly/Ser residues. We used TEV enzyme (MoBiTech) to digest 4HDS(+) protein and removed His-Tag sequence following the standard digestion and purification protocol. The Tev cleavage produced protein, called 4HDS (-). The amino acid sequence of 4HDS(-) is shown in SEQ ID NO: 11.

(8). Preparation of X03 with His-Tag (X03 (+))—The same procedures as described for cloning the 4HDS(+) may be used to prepare X03 (+) which contains 4 tandem repeats of the Z domain preceded by a histine tag and a Tev cleavage site. The X03 DNA is subcloned into the parent pETM-11 vector that contains a $(His)_6$ tag and 10 additional residues (P M S D Y D I P T T) (SEQ ID NO: 20) between the histidine tag and the Tev cleavage sequence. No specific anchor or linker sequence was engineered into this construct.

The amino acid sequence of X03 (+) is shown in SEQ ID NO: 12.

(9). Preparation of X03 without His Tag (X03 (-))—We used TEV enzyme (MoBiTech) to digest the X03(+) protein and removed His-Tag sequence following the standard digestion and purification protocol. The resulting protein is called X03(-). The amino acid sequence of X03 (-) is shown in SEQ ID NO: 13.

(10). Immobilization of 4HDS (-) on Beads—A mixture in which 11 ml of PB and 200 mg of 4HDS(-) were dispersed in 100 ml of a 0.1 M phosphate buffer (pH: 6.8) was prepared. After the addition of 21 g of sodium sulfate, the mixture was shaken at 25° C. for 24 hours so that 4HDS(-) was immobilized to PB. The resulting beads were filtered, mixed with 100 ml of 5 M thioglycerol, and reacted at 30° C. for 4 hours to block the remaining epoxy groups. The beads were washed with PBS/0.05% Tween 20, and washed with PBS to obtain 11 ml of 4HDS(-)-immobilized porous beads (4HDS(-)-PB).

(11). Immobilization of X03 (-) on Beads—X03(-) immobilized beads (X03(-)-PB) were obtained in the same manner as described in above Immobilization Example, except for using X03(-) instead of 4HDS(-).

(12). Measurement of Dynamic Binding Capacity (DBC)—DBC measurement was done with "ÄKTAprime plus" (GE Healthcare) chromatography system. Columns (inner diameter: 0.5 cm) were respectively packed with HDS(-)-PB, X03(-)-PB, or MabSelect SuRe (GE Healthcare) to a bed height of 20 cm. After equilibrating each column using a 20 mM phosphate buffer (pH: 7.4), a 20 mM phosphate buffer (pH: 7.4) including human polyclonal IgG (5 mg/ml) was allowed to pump into each column at a linear flow rate of 300 cm/h. The DBC was calculated at 10% breakthrough. The initial DBC without alkali treatment for 4HDS(-)-PB, X03 (-)-PB, and Mabselect SuRe was, 46 mg/mL, 45 mg/mL, and 42 mg/mL, respectively.

(13). Measurement of Alkaline Resistance—Each column used in Measurement Example 1 was installed in an "ÄKTAprime plus" instrument, and 40 ml of 0.5N sodium hydroxide was allowed to flow through each column. Each column was removed from the apparatus, sealed, and allowed to stand at room temperature for a given time (0.5N NaOH soak experiment), then washed with 20 mM phosphate buffer (pH: 7.4). The DBC after 0.5N sodium hydroxide soak was measured in the same manner as in above Measurement of Dynamic Binding. The DBC retention ratio against 0.5N sodium hydroxide treatment time was shown in FIG. 3. As shown in FIG. 3, the affinity matrix 4HDS(-)-PB has a significant improved performance on DBC retention ratio after alkali treatment than X03(-)-PB, and even than MabSelect SuRe, the best known commercial alkali resistant Protein A affinity matrix.

We claim:

1. An Ig-binding protein comprising the peptide sequence selected from the group consisting of SEQ ID NO: 2, 3, 4, 5, 6, 7, 8, 9, 10, 11, and 14.

2. The Ig-binding protein of claim 1, comprising the peptide sequence of SEQ ID NO: 2.

3. The Ig-binding protein of claim 1, comprising the peptide sequence of SEQ ID NO: 3.

4. The Ig-binding protein of claim 1, comprising the peptide sequence of SEQ ID NO: 4.

5. The Ig-binding protein of claim 1, comprising the peptide sequence of SEQ ID NO: 5.

6. The Ig-binding protein of claim 1, comprising the peptide sequence of SEQ ID NO: 6.

7. The Ig-binding protein of claim 1, comprising the peptide sequence of SEQ ID NO: 7.

8. The Ig-binding protein of claim 1, comprising the peptide sequence of SEQ ID NO: 8.

9. The Ig-binding protein of claim 1, comprising the peptide sequence of SEQ ID NO: 9.

10. The Ig-binding protein of claim 1, comprising the peptide sequence of SEQ ID NO: 10.

11. The Ig-binding protein of claim 1, comprising the peptide sequence of SEQ ID NO: 11.

12. The Ig-binding protein of claim 1, comprising the peptide sequence of SEQ ID NO: 14.

13. A matrix, comprising:
the Ig-binding protein of claim 1 coupled to a solid support.

14. The matrix of claim 13,
wherein the Ig-binding protein is coupled to the solid support through a linker peptide.

15. The matrix of claim 14,
wherein the linker peptide comprises the amino acid sequence of SEQ ID NO: 15.

16. The matrix of claim 13, wherein the Ig-binding protein comprises the peptide sequence of SEQ ID NO: 2.

17. The matrix of claim 13, wherein the Ig-binding protein comprises the peptide sequence of SEQ ID NO: 3.

18. The matrix of claim 13, wherein the Ig-binding protein comprises the peptide sequence of SEQ ID NO: 4.

19. The matrix of claim 13, wherein the Ig-binding protein comprises the peptide sequence of SEQ ID NO: 5.

20. The matrix of claim 13, wherein the Ig-binding protein comprises the peptide sequence of SEQ ID NO: 6.

21. The matrix of claim 13, wherein the Ig-binding protein comprises the peptide sequence of SEQ ID NO: 7.

22. The matrix of claim 13, wherein the Ig-binding protein comprises the peptide sequence of SEQ ID NO: 8.

23. The matrix of claim 13, wherein the Ig-binding protein comprises the peptide sequence of SEQ ID NO: 9.

24. The matrix of claim 13, wherein the Ig-binding protein comprises the peptide sequence of SEQ ID NO: 10.

25. The matrix of claim 13, wherein the Ig-binding protein comprises the peptide sequence of SEQ ID NO: 11.

26. The matrix of claim 13, wherein the Ig-binding protein comprises the peptide sequence of SEQ ID NO: 14.

27. A method of separating an immunoglobulin from a composition, the method comprising:
contacting the composition with the matrix of claim 13, thereby separating the immunoglobulin from another substance,
wherein the composition comprises the immunoglobulin and the other substance.

\* \* \* \* \*

SEQUENCE LISTING

<160> NUMBER OF SEQ ID NOS: 20

<210> SEQ ID NO 1
<211> LENGTH: 58
<212> TYPE: PRT
<213> ORGANISM: Artificial Sequence
<220> FEATURE:
<223> OTHER INFORMATION: Synthetic peptide

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 2
<211> LENGTH: 58
<212> TYPE: PRT
<213> ORGANISM: Artificial Sequence
<220> FEATURE:
<223> OTHER INFORMATION: Synthetic peptide

<400> SEQUENCE: 2

Val Asp His Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 3
<211> LENGTH: 58
<212> TYPE: PRT
<213> ORGANISM: Artificial Sequence
<220> FEATURE:
<223> OTHER INFORMATION: Synthetic peptide

<400> SEQUENCE: 3

Val Asp Ser Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 4
<211> LENGTH: 58
<212> TYPE: PRT
<213> ORGANISM: Artificial Sequence
<220> FEATURE:
<223> OTHER INFORMATION: Synthetic peptide

<400> SEQUENCE: 4

Val Asp Asn Lys Phe Asn Lys Glu Gln Gln Asn Ala Phe Tyr Glu Ile
1               5                   10                  15

Leu His Leu Pro Asn Leu His Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 5
<211> LENGTH: 58
<212> TYPE: PRT
<213> ORGANISM: Artificial Sequence
<220> FEATURE:
<223> OTHER INFORMATION: Synthetic peptide

<400> SEQUENCE: 5

Val Asp Asn Lys Phe Asn Lys Glu Gln Gln Asn Ala Phe Tyr Glu Ile
1               5                   10                  15

Leu His Leu Pro Asn Leu Ser Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Synthetic peptide

<400> SEQUENCE: 6

Val Asp His Lys Phe Asn Lys Glu Gln Gln Asn Ala Phe Tyr Glu Ile
1               5                   10                  15

Leu His Leu Pro Asn Leu Ser Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: Synthetic peptide

<400> SEQUENCE: 7

Val Asp His Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Synthetic peptide

<400> SEQUENCE: 8

Val Asp His Lys Phe Asp Lys Glu Gln Gln Asn Ala Phe Tyr Glu Ile
1               5                   10                  15

```
Leu His Leu Pro Asn Leu Ser Glu Glu Gln Arg Asn Ala Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
            50                  55
```

<210> SEQ ID NO 9  
<211> LENGTH: 245  
<212> TYPE: PRT  
<213> ORGANISM: Artificial Sequence  
<220> FEATURE:  
<223> OTHER INFORMATION: Synthetic peptide

<400> SEQUENCE: 9

```
Met Ala Thr Lys Ala Ser Lys Val Asp His Lys Phe Asp Lys Glu Gln
1               5                   10                  15

Gln Asn Ala Phe Tyr Glu Ile Leu His Leu Pro Asn Leu Ser Glu Glu
            20                  25                  30

Gln Arg Asn Ala Phe Ile Gln Ser Leu Lys Asp Asp Pro Ser Gln Ser
            35                  40                  45

Ala Asn Leu Leu Ala Glu Ala Lys Lys Leu Asn Asp Ala Gln Ala Pro
        50                  55                  60

Lys Glu Phe Val Asp His Lys Phe Asp Lys Glu Gln Gln Asn Ala Phe
65              70                  75                  80

Tyr Glu Ile Leu His Leu Pro Asn Leu Ser Glu Glu Gln Arg Asn Ala
                85                  90                  95

Phe Ile Gln Ser Leu Lys Asp Asp Pro Ser Gln Ser Ala Asn Leu Leu
            100                 105                 110

Ala Glu Ala Lys Lys Leu Asn Asp Ala Gln Ala Pro Lys Glu Phe Val
            115                 120                 125

Asp His Lys Phe Asp Lys Glu Gln Gln Asn Ala Phe Tyr Glu Ile Leu
        130                 135                 140

His Leu Pro Asn Leu Ser Glu Glu Gln Arg Asn Ala Phe Ile Gln Ser
145                 150                 155                 160

Leu Lys Asp Asp Pro Ser Gln Ser Ala Asn Leu Leu Ala Glu Ala Lys
                165                 170                 175

Lys Leu Asn Asp Ala Gln Ala Pro Lys Glu Phe Val Asp His Lys Phe
            180                 185                 190

Asp Lys Glu Gln Gln Asn Ala Phe Tyr Glu Ile Leu His Leu Pro Asn
            195                 200                 205

Leu Ser Glu Glu Gln Arg Asn Ala Phe Ile Gln Ser Leu Lys Asp Asp
        210                 215                 220

Pro Ser Gln Ser Ala Asn Leu Leu Ala Glu Ala Lys Lys Leu Asn Asp
225                 230                 235                 240

Ala Gln Ala Pro Lys
                245
```

<210> SEQ ID NO 10  
<211> LENGTH: 260  
<212> TYPE: PRT  
<213> ORGANISM: Artificial Sequence  
<220> FEATURE:  
<223> OTHER INFORMATION: Synthetic peptide

<400> SEQUENCE: 10

```
Met Lys His His His His His His Glu Asn Leu Tyr Phe Gln Gly
1               5                   10                  15
```

```
Ala Thr Lys Ala Ser Lys Val Asp His Lys Phe Asp Lys Glu Gln Gln
            20                  25                  30

Asn Ala Phe Tyr Glu Ile Leu His Leu Pro Asn Leu Ser Glu Glu Gln
            35                  40                  45

Arg Asn Ala Phe Ile Gln Ser Leu Lys Asp Asp Pro Ser Gln Ser Ala
 50                  55                  60

Asn Leu Leu Ala Glu Ala Lys Lys Leu Asn Asp Ala Gln Ala Pro Lys
 65                  70                  75                  80

Glu Phe Val Asp His Lys Phe Asp Lys Glu Gln Gln Asn Ala Phe Tyr
                 85                  90                  95

Glu Ile Leu His Leu Pro Asn Leu Ser Glu Glu Gln Arg Asn Ala Phe
            100                 105                 110

Ile Gln Ser Leu Lys Asp Asp Pro Ser Gln Ser Ala Asn Leu Leu Ala
            115                 120                 125

Glu Ala Lys Lys Leu Asn Asp Ala Gln Ala Pro Lys Glu Phe Val Asp
130                 135                 140

His Lys Phe Asp Lys Glu Gln Gln Asn Ala Phe Tyr Glu Ile Leu His
145                 150                 155                 160

Leu Pro Asn Leu Ser Glu Glu Gln Arg Asn Ala Phe Ile Gln Ser Leu
                165                 170                 175

Lys Asp Asp Pro Ser Gln Ser Ala Asn Leu Leu Ala Glu Ala Lys Lys
            180                 185                 190

Leu Asn Asp Ala Gln Ala Pro Lys Glu Phe Val Asp His Lys Phe Asp
            195                 200                 205

Lys Glu Gln Gln Asn Ala Phe Tyr Glu Ile Leu His Leu Pro Asn Leu
    210                 215                 220

Ser Glu Glu Gln Arg Asn Ala Phe Ile Gln Ser Leu Lys Asp Asp Pro
225                 230                 235                 240

Ser Gln Ser Ala Asn Leu Leu Ala Glu Ala Lys Lys Leu Asn Asp Ala
                245                 250                 255

Gln Ala Pro Lys
            260

<210> SEQ ID NO 11
<211> LENGTH: 245
<212> TYPE: PRT
<213> ORGANISM: Artificial Sequence
<220> FEATURE:
<223> OTHER INFORMATION: Synthetic peptide

<400> SEQUENCE: 11

Gly Ala Thr Lys Ala Ser Lys Val Asp His Lys Phe Asp Lys Glu Gln
 1               5                  10                  15

Gln Asn Ala Phe Tyr Glu Ile Leu His Leu Pro Asn Leu Ser Glu Glu
             20                  25                  30

Gln Arg Asn Ala Phe Ile Gln Ser Leu Lys Asp Asp Pro Ser Gln Ser
         35                  40                  45

Ala Asn Leu Leu Ala Glu Ala Lys Lys Leu Asn Asp Ala Gln Ala Pro
 50                  55                  60

Lys Glu Phe Val Asp His Lys Phe Asp Lys Glu Gln Gln Asn Ala Phe
 65                  70                  75                  80

Tyr Glu Ile Leu His Leu Pro Asn Leu Ser Glu Glu Gln Arg Asn Ala
                 85                  90                  95

Phe Ile Gln Ser Leu Lys Asp Asp Pro Ser Gln Ser Ala Asn Leu Leu
            100                 105                 110
```

```
Ala Glu Ala Lys Lys Leu Asn Asp Ala Gln Ala Pro Lys Glu Phe Val
            115                 120                 125

Asp His Lys Phe Asp Lys Glu Gln Gln Asn Ala Phe Tyr Glu Ile Leu
130                 135                 140

His Leu Pro Asn Leu Ser Glu Glu Gln Arg Asn Ala Phe Ile Gln Ser
145                 150                 155                 160

Leu Lys Asp Asp Pro Ser Gln Ser Ala Asn Leu Leu Ala Glu Ala Lys
                165                 170                 175

Lys Leu Asn Asp Ala Gln Ala Pro Lys Glu Phe Val Asp His Lys Phe
            180                 185                 190

Asp Lys Glu Gln Gln Asn Ala Phe Tyr Glu Ile Leu His Leu Pro Asn
        195                 200                 205

Leu Ser Glu Glu Gln Arg Asn Ala Phe Ile Gln Ser Leu Lys Asp Asp
    210                 215                 220

Pro Ser Gln Ser Ala Asn Leu Leu Ala Glu Ala Lys Lys Leu Asn Asp
225                 230                 235                 240

Ala Gln Ala Pro Lys
                245

<210> SEQ ID NO 12
<211> LENGTH: 264
<212> TYPE: PRT
<213> ORGANISM: Artificial Sequence
<220> FEATURE:
<223> OTHER INFORMATION: Synthetic peptide

<400> SEQUENCE: 12

Met Lys His His His His His Pro Met Ser Asp Tyr Asp Ile Pro Thr
1               5                   10                  15

Thr Glu Asn Leu Tyr Phe Gln Gly Ala Met Val Asp Asn Lys Phe Asn
            20                  25                  30

Lys Glu Gln Gln Asn Ala Phe Tyr Glu Ile Leu His Leu Pro Asn Leu
        35                  40                  45

Asn Glu Glu Gln Arg Asn Ala Phe Ile Gln Ser Leu Lys Asp Asp Pro
    50                  55                  60

Ser Gln Ser Ala Asn Leu Leu Ala Glu Ala Lys Lys Leu Asn Asp Ala
65                  70                  75                  80

Gln Ala Pro Lys Glu Phe Val Asp Asn Lys Phe Asn Lys Glu Gln Gln
                85                  90                  95

Asn Ala Phe Tyr Glu Ile Leu His Leu Pro Asn Leu Asn Glu Glu Gln
            100                 105                 110

Arg Asn Ala Phe Ile Gln Ser Leu Lys Asp Asp Pro Ser Gln Ser Ala
        115                 120                 125

Asn Leu Leu Ala Glu Ala Lys Lys Leu Asn Asp Ala Gln Ala Pro Lys
    130                 135                 140

Glu Phe Val Asp Asn Lys Phe Asn Lys Glu Gln Gln Asn Ala Phe Tyr
145                 150                 155                 160

Glu Ile Leu His Leu Pro Asn Leu Asn Glu Glu Gln Arg Asn Ala Phe
                165                 170                 175

Ile Gln Ser Leu Lys Asp Asp Pro Ser Gln Ser Ala Asn Leu Leu Ala
            180                 185                 190

Glu Ala Lys Lys Leu Asn Asp Ala Gln Ala Pro Lys Glu Phe Val Asp
        195                 200                 205

Asn Lys Phe Asn Lys Glu Gln Gln Asn Ala Phe Tyr Glu Ile Leu His
    210                 215                 220
```

Leu Pro Asn Leu Asn Glu Glu Gln Arg Asn Ala Phe Ile Gln Ser Leu
225                 230                 235                 240

Lys Asp Asp Pro Ser Gln Ser Ala Asn Leu Leu Ala Glu Ala Lys Lys
            245                 250                 255

Leu Asn Asp Ala Gln Ala Pro Lys
            260

<210> SEQ ID NO 13
<211> LENGTH: 241
<212> TYPE: PRT
<213> ORGANISM: Artificial Sequence
<220> FEATURE:
<223> OTHER INFORMATION: Synthetic peptide

<400> SEQUENCE: 13

Gly Ala Met Val Asp Asn Lys Phe Asn Lys Glu Gln Gln Asn Ala Phe
1               5                   10                  15

Tyr Glu Ile Leu His Leu Pro Asn Leu Asn Glu Glu Gln Arg Asn Ala
            20                  25                  30

Phe Ile Gln Ser Leu Lys Asp Asp Pro Ser Gln Ser Ala Asn Leu Leu
        35                  40                  45

Ala Glu Ala Lys Lys Leu Asn Asp Ala Gln Ala Pro Lys Glu Phe Val
    50                  55                  60

Asp Asn Lys Phe Asn Lys Glu Gln Gln Asn Ala Phe Tyr Glu Ile Leu
65                  70                  75                  80

His Leu Pro Asn Leu Asn Glu Glu Gln Arg Asn Ala Phe Ile Gln Ser
                85                  90                  95

Leu Lys Asp Asp Pro Ser Gln Ser Ala Asn Leu Leu Ala Glu Ala Lys
            100                 105                 110

Lys Leu Asn Asp Ala Gln Ala Pro Lys Glu Phe Val Asp Asn Lys Phe
        115                 120                 125

Asn Lys Glu Gln Gln Asn Ala Phe Tyr Glu Ile Leu His Leu Pro Asn
    130                 135                 140

Leu Asn Glu Glu Gln Arg Asn Ala Phe Ile Gln Ser Leu Lys Asp Asp
145                 150                 155                 160

Pro Ser Gln Ser Ala Asn Leu Leu Ala Glu Ala Lys Lys Leu Asn Asp
                165                 170                 175

Ala Gln Ala Pro Lys Glu Phe Val Asp Asn Lys Phe Asn Lys Glu Gln
            180                 185                 190

Gln Asn Ala Phe Tyr Glu Ile Leu His Leu Pro Asn Leu Asn Glu Glu
        195                 200                 205

Gln Arg Asn Ala Phe Ile Gln Ser Leu Lys Asp Pro Ser Gln Ser
    210                 215                 220

Ala Asn Leu Leu Ala Glu Ala Lys Lys Leu Asn Asp Ala Gln Ala Pro
225                 230                 235                 240

Lys

<210> SEQ ID NO 14
<211> LENGTH: 58
<212> TYPE: PRT
<213> ORGANISM: Artificial Sequence
<220> FEATURE:
<223> OTHER INFORMATION: Synthetic peptide

<400> SEQUENCE: 14

Val Asp Asn Lys Phe Asp Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
                35                  40                  45

Lys Lys Leu Asn Asp Ala Gln Ala Pro Lys
        50                  55

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Ala Thr Lys Ala Ser Lys
1               5

<210> SEQ ID NO 16
<211> LENGTH: 20
<212> TYPE: DNA
<213> ORGANISM: Artificial  Sequence
<220> FEATURE:
<223> OTHER INFORMATION: Synthetic primer

<400> SEQUENCE: 16
taatacgact cactataggg                                            20

<210> SEQ ID NO 17
<211> LENGTH: 19
<212> TYPE: DNA
<213> ORGANISM: Artificial  Sequence
<220> FEATURE:
<223> OTHER INFORMATION: Synthetic primer

<400> SEQUENCE: 17
gctagttatt gctcagcgg                                             19

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Glu Asn Leu Tyr Phe Gln Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa is Gly or Ser

<400> SEQUENCE: 19

Glu Asn Leu Tyr Phe Gln Xaa
1               5

<210> SEQ ID NO 20

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Pro Met Ser Asp Tyr Asp Ile Pro Thr Thr
1               5                   10
```